United States Patent
Filippi et al.

(10) Patent No.: US 6,875,892 B2
(45) Date of Patent: Apr. 5, 2005

(54) METHOD FOR THE PRODUCTION OF UREA

(75) Inventors: Ermanno Filippi, Castagnola (CH); Domenico Romiti, Lugano (CH)

(73) Assignee: Urea Casale S.A. (CH)

( * ) Notice: Subject to any disclaimer, the term of this patent is extended or adjusted under 35 U.S.C. 154(b) by 0 days.

(21) Appl. No.: 10/472,067
(22) PCT Filed: Mar. 8, 2002
(86) PCT No.: PCT/EP02/02591
§ 371 (c)(1), (2), (4) Date: Mar. 26, 2004
(87) PCT Pub. No.: WO02/074734
PCT Pub. Date: Sep. 26, 2002

(65) Prior Publication Data
US 2004/0152918 A1 Aug. 5, 2004

(30) Foreign Application Priority Data
Mar. 16, 2001 (EP) .......................................... 011066495

(51) Int. Cl.⁷ ...................... C07C 273/02; C07C 273/04
(52) U.S. Cl. ............................. 564/67; 564/70; 564/71; 564/72
(58) Field of Search .............................. 564/67, 70, 71, 564/72

(56) References Cited

U.S. PATENT DOCUMENTS

| 4,590,044 | A | 5/1986 | Mos et al. | |
|---|---|---|---|---|
| 6,287,525 | B1 | * 9/2001 | Pagani | ....................... 422/234 |
| 6,632,967 | B2 | * 10/2003 | Scholten et al. | .............. 564/67 |

FOREIGN PATENT DOCUMENTS

| EP | 0 495 418 A1 | 7/1992 |
|---|---|---|
| WO | WO-95/31278 A1 | 11/1995 |

* cited by examiner

Primary Examiner—Peter O'Sullivan
(74) Attorney, Agent, or Firm—Akerman Senterfirr

(57) ABSTRACT

A method for the production of synthesis urea from liquid ammonia and gaseous carbon dioxide, comprising the step of feeding separate flows (6, 8) of liquid ammonia and gaseous carbon dioxide in continuous to a substantially vertical or horizontal column synthesis reactor (1), is distinguished in that the feed of liquid ammonia is split up into at least two consecutive sections (Z1–Z7) of said column.

3 Claims, 1 Drawing Sheet

METHOD FOR THE PRODUCTION OF UREA

DESCRIPTION

1. Field of Application

The present invention relates to a method for the continuous production of synthesis urea from liquid ammonia and gaseous carbon dioxide, fed continuously into a vertical or horizontal column synthesis reactor.

This invention also relates to a synthesis reactor for carrying out the aforesaid method.

2. Prior Art

As known, urea synthesis from ammonia and carbon dioxide substantially occurs through two reactions: a first reaction in which carbamate is produced and a second reaction in which the carbamate just produced is decomposed in urea and water.

The first reaction is very fast and strongly exothermal; the second reaction, i.e. the decomposition reaction, is endothermic; the amount of heat needed to complete the carbamate decomposition is quite smaller than that generated and provided by the formation reaction of the carbamate itself. Accordingly, the urea synthesis reaction is considerably exothermal in its whole. Moreover, the large amount of heat, which is also generated in a short period of time, is such to determine a quick evaporation of a relevant amount of the liquid ammonia fed into the synthesis reactor in a urea production process of the type under consideration.

In the vapour phase, ammonia does not react with carbon dioxide to produce carbamate and is discharged from the reactor, as unreacted component, in a gaseous flow further comprising unreacted products and possible gaseous by-products of the reaction.

When the aforesaid synthesis urea production is realised on an industrial scale, where it is essential to achieve an acceptable yield, on one end it is necessary to control the exothermal degree of the first reaction, so to limit as much as possible the evaporation of liquid ammonia. On the other end, it is necessary to recover almost all of the unreacted ammonia, bringing it again to the liquid state and recycling it to the reactor. Usually, these two tasks are achieved by transforming the liquid ammonia into carbamate (through reaction with carbon dioxide) and recycling the so obtained carbamate to the synthesis reactor.

In order to achieve an acceptable yield from the industrial point of view, the aforesaid operations must be repeated in continuous, in specific apparatuses provided downstream of the synthesis reactor.

Beside the technical/operating complexity of the aforesaid operations, the recognised burdens in terms of costs of the apparatuses required to carry them out and for the operating and maintenance of such apparatuses, remarkably affect the synthesis urea production costs in the process under consideration.

The technical problem underlying the present invention is that of providing a method for synthesis urea production from liquid ammonia and gaseous carbon dioxide, based on functional features that allow to increase the production yield with respect to the prior art in such a way to substantially reduce, if not even cancel, the need of heavily intervening downstream of the synthesis reactor, for carrying out the above mentioned uneconomic recovery and recycle operations of the unreacted ammonia.

SUMMARY OF THE INVENTION

According to the present invention, this problem is solved by a method for synthesis urea production of the aforesaid kind comprising the step of feeding separate flows of liquid ammonia and gaseous carbon dioxide, respectively, in continuous to a substantially vertical or horizontal column synthesis reactor, characterized in that the feed of liquid ammonia is split up into at least two consecutive sections of said column.

Preferably, the separate flows of liquid ammonia and gaseous carbon dioxide are fed in co-current into the synthesis reactor.

In the method according to the present invention it is further contemplated the possibility of splitting also the gaseous carbon dioxide feed into said at least two consecutive sections of the synthesis column.

The present invention is based upon the surprising finding that, by splitting the liquid ammonia feed into at least two consecutive sections of the column synthesis reactor, the conversion yield of carbon dioxide and ammonia into urea in the reactor is considerably improved if compared to the yield in the reactor that can be obtained by the conventional methods for urea production, all the other operating conditions being the same.

In fact, with the method according to the present invention, the conversion yield into urea in the reactor is higher than 70% whereas in the conventional methods such yield is limited to a value lower than 70%, all the other operating conditions being the same.

Among the conventional methods for which the urea conversion yield is limited as indicated above, there are comprised the conventional methods wherein liquid ammonia and gaseous carbon dioxide are fed into the reactor as raw materials and a large part of the conventional methods wherein unreacted recycle materials are also fed to the reactor, such as ammonia and carbon dioxide in gaseous phase and carbamate aqueous solutions.

In particular, it has been found that the splitting of the liquid ammonia feed into at least two consecutive sections of the synthesis reactor advantageously allows an effective control of the exothermal degree of the first synthesis reaction of urea. It follows a more homogeneous distribution of the heat generated during such first reaction along the reactor column.

In this way, the evaporation of liquid ammonia inside the synthesis reactor is markedly reduced to all advantage of a greater urea conversion efficiency. In fact, the content of gaseous ammonia in the reactor is reduced. As already mentioned, such gaseous ammonia is no more capable of reacting with carbon dioxide to give carbamate.

Accordingly, also the investment and maintenance costs of the plants as well as the operating costs for carrying out the recovery and recycle to the reactor of unreacted components are markedly reduced as the increase of the urea conversion effectiveness attained with the method of the present invention implies a remarkable reduction of the amount of such unreacted components.

The present invention also relates to a reactor for the production in continuous of urea from gaseous carbon dioxide and liquid ammonia, having the shape of a column with horizontal or vertical longitudinal axis and a predetermined crossing direction, comprising a shell provided with opposite bottoms, an inlet opening for a flow comprising gaseous carbon dioxide an inlet opening for a flow of liquid ammonia, an outlet opening for a liquid flow comprising urea, characterized in that it further comprises means for splitting the feed of liquid ammonia into at least two consecutive sections of the column.

Preferably, the means for splitting the feed of liquid ammonia comprises at least one inner duct, which extends from the inlet opening for the flow of liquid ammonia and passes through said at least two consecutive sections of the column, and means for distributing or injecting the liquid ammonia arranged in predetermined positions of said at least one duct in each of said at least two consecutive sections.

According to a preferred embodiment of the present invention, the method for producing urea in continuous comprises the steps of:

providing a reactor having the shape of a column with a horizontal or vertical longitudinal axis and a predetermined crossing direction, comprising a shell provided with opposite bottoms, an inlet opening for a flow comprising gaseous carbon dioxide, an inlet opening for a flow of liquid ammonia, an outlet opening for a liquid flow comprising urea, at least one inner duct which extends from the inlet opening for the flow of liquid ammonia and that passes through at least two consecutive sections of the column and means for distributing or injecting liquid ammonia arranged in predetermined positions of said at least one duct in each one of said at least two consecutive sections, feeding in continuous in do-current said flow of gaseous carbon dioxide and said flow of liquid ammonia to the reactor, making said flow of gaseous carbon dioxide advance in the reactor in such a way that it passes through each of said at least two consecutive sections, making said flow of liquid ammonia advance in said at least one duct as well as distributing and injecting the liquid ammonia in each one of said at least two consecutive sections, the liquid ammonia reacting thus with the gaseous carbon dioxide in each one of said at least two consecutive sections, and discharging in continuous from the reactor said liquid flow comprising urea.

The features and the advantages of the invention will become clearer from the following description of an indicative and non-limiting example of a preferred embodiment thereof, made with reference to the attached drawing.

DETAILED DESCRIPTION

Figure 1:
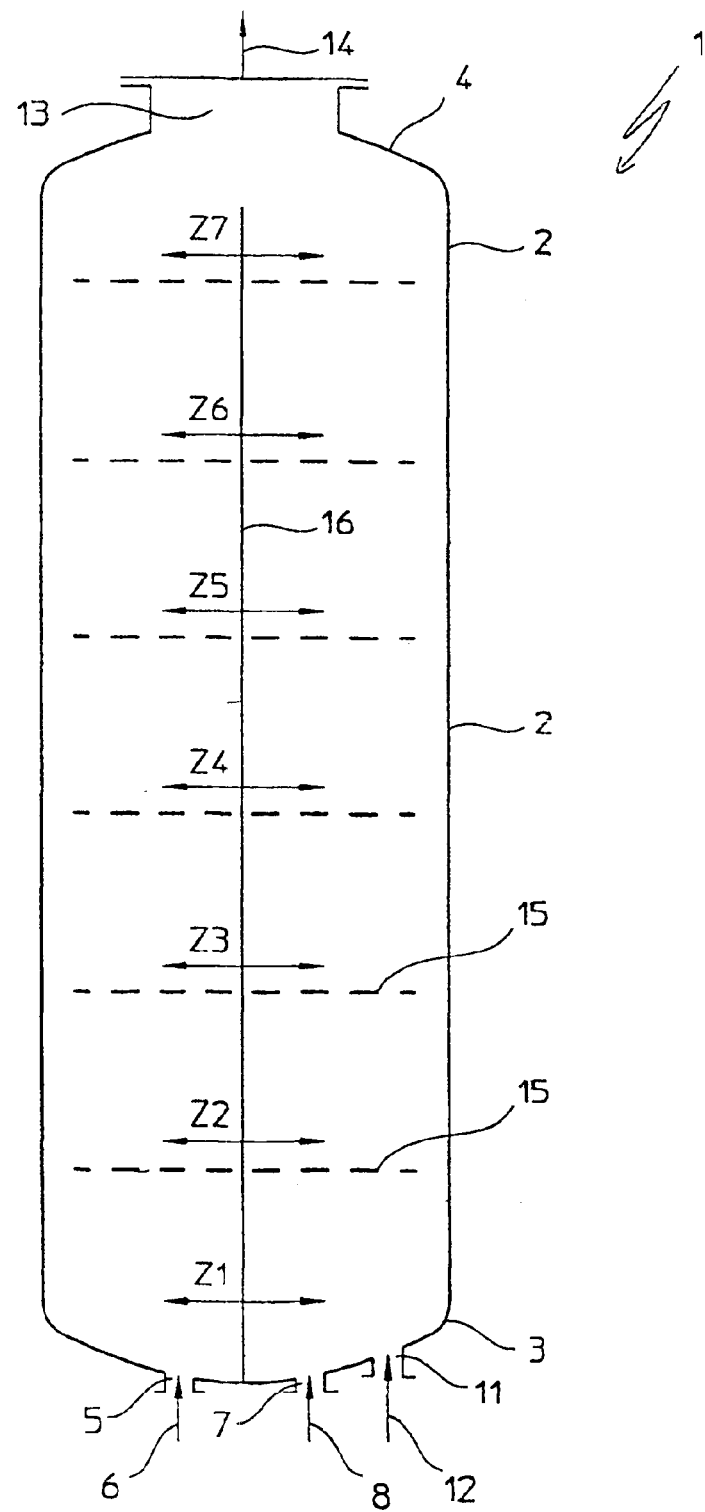
FIG. 1 shows schematically a synthesis reactor for carrying out the method for producing urea in continuous according to the present invention.

With reference to the attached figure, with numeral 1 there is indicated in its whole a synthesis reactor for the production of urea in continuous.

Reactor 1 has the shape of a column with a vertical longitudinal axis and comprises a shell 2 provided, at its opposite ends, with a lower bottom 3 and an upper bottom 4.

Usually, the reactor 1 operates at a temperature comprised in the range from 220 to 340° C. and at a pressure of 120–400 bar.

Reactor 1 further comprises, at the lower bottom 3, an inlet opening 5 for a flow 6 comprising gaseous carbon dioxide, an inlet opening 7 for a flow 8 of liquid ammonia, and an inlet opening 11 for a flow 12 formed by a recycled carbamate solution.

The liquid flows 8, 12 and the gaseous flow 6 are fed in co-current and pass through the reactor 1 upwards, that is to say from the lower bottom 3 to the upper bottom 4.

At its upper bottom 4, the reactor 1 further comprises an outlet opening 13 for a flow 14 of an aqueous solution comprising urea together with unreacted substances, in particular carbamate and ammonia.

Reactor 1 further comprises a plurality of perforated trays 15 (in the example six trays) arranged horizontally at different heights and preferably equidistant from each other.

In particular, the perforated trays 15 define a plurality of consecutive reaction sections in the reactor 1 (in the example seven consecutive sections), each section being delimited in its lower portion by a perforated tray 15 or by the lower bottom 3 of the reactor 1.

The perforated trays 15 are per se conventional and advantageously allow an intimate mixing between the liquid flows and the gaseous flows flowing in co-current in the reactor 1 from the lower bottom 3 to the upper bottom 4.

In the present embodiment, in the reactor 1 there are defined: a lower end reaction section Z1, delimited in its lower part by the lower bottom 3 and in its upper part by a tray 15; five intermediate reaction sections Z2, Z3, Z4, Z5 and Z6, delimited in their lower and upper parts by a pair of consecutive trays 15, respectively; as well as an upper end reaction section Z7, delimited in its lower part by a tray 15 and in its upper part by the upper bottom 4.

According to the present invention, in the example shown in the figure, the reactor 1 further comprises a substantially central inner duct 16, which extends vertically from the inlet opening 7 and passes through the lower end reaction section Z1, the intermediate reaction sections Z2–Z6 and partially the upper end reaction section Z7.

The duct 16 is flown by the flow 8 of liquid ammonia and is equipped with distributing or injecting means (for example nozzle distributors) arranged in predetermined positions thereof so as to split the liquid ammonia into each one of the consecutive reaction sections Z1–Z7.

In particular, in the present embodiment, the means for distributing and injecting the feed liquid ammonia inside the reactor 1 is arranged in each section Z1–Z7, spaced apart from the duct 16 as schematically indicated by the arrows.

With the present invention, a substantial distribution along the reactor 1 of the reaction heat generated by the first exothermal carbamate formation reaction is attained, by providing the contact between the reactants, i.e. liquid ammonia and gaseous carbon dioxide, fed separately and in co-current to the reactor 1 in a plurality of distinct sections thereof.

Such a distribution allows a suitable control of the exothermal degree of the first reaction and advantageously limits the evaporation of liquid ammonia thus increasing the conversion yield of carbon dioxide and ammonia into urea.

Numerous modifications and variations of the synthesis reactor can be made by the skilled person, all falling within the: scope of protection of the present invention, as defined by the following claims, in order to meet incidental and specific requirements.

For example, the number of consecutive reaction sections into which the liquid ammonia feed shall be split as well as the shape and number of ducts internal to the reactor provided with associated means for distributing or injecting liquid ammonia in said sections, can vary at will according to the specific requirements.

Further on, instead of the previously illustrated solution that provides an inner duct with associated liquid ammonia distributing means, the splitting of liquid ammonia into the consecutive reaction sections may be carried out by providing one or more inlet openings of the liquid ammonia feed into the reactor in each one of said sections.

What is claimed is:

1. Method for the production of synthesis urea from liquid ammonia and gaseous carbon dioxide, comprising the step of feeding separate flows (6, 8) of liquid ammonia and gaseous carbon dioxide, respectively, in continuous to a substantially vertical or horizontal column synthesis reactor (1), characterized in that the feed of liquid ammonia is split up into at least two consecutive sections (z1–Z7) of said column.

2. Method according to claim 1, characterized in that the feed of gaseous carbon dioxide is split up into said consecutive sections (Z1–Z7) of the column.

3. Method for producing synthesis urea from gaseous carbon dioxide and liquid ammonia, comprising the steps of;

providing a reactor (1) having the shape of a column with a horizontal or vertical longitudinal axis and a predetermined crossing direction, comprising a shell (2) provided with opposite bottoms (3, 4), an inlet opening (5) for a flow (6) comprising gaseous carbon dioxide, an inlet opening (7) for a flow (8) of liquid ammonia, an outlet opening (13) for a liquid flow (14) comprising urea, at least one inner duct (16), which extends from the inlet opening (7) for the flow (8) of liquid ammonia and passes through at least two consecutive sections (Z1–Z7) of the column and means for distributing or injecting liquid ammonia arranged in predetermined positions of said at least one duct (16) in each one of said at least two consecutive sections (Z1–Z7), feeding in continuous in co-current said flow (6) of gaseous carbon dioxide and said flow (8) of liquid ammonia in the reactor (1), making said flow (6) of gaseous carbon dioxide advance in the reactor (1) in such a way that it passes through each of said at least two consecutive sections (Z1–Z7), making said flow (8) of liquid ammonia advance in said at least one duct (16), and distributing and injecting the liquid ammonia in each one of said at least two consecutive: sections (Z1–Z7), the liquid ammonia reacting thus with the gaseous carbon dioxide in each one of said at least two consecutive sections (Z1–Z7), and discharging in continuous from the reactor (1) said liquid flow (14) comprising urea.

* * * * *